(12) United States Patent
Watanabe et al.

(10) Patent No.: US 9,155,835 B2
(45) Date of Patent: Oct. 13, 2015

(54) MEDICAMENT DISPENSING DEVICE

(75) Inventors: Atsushi Watanabe, Ehime (JP); Seiji Kikuchi, Ehime (JP); Tsuguhiro Kondo, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 421 days.

(21) Appl. No.: 13/141,154

(22) PCT Filed: Oct. 20, 2009

(86) PCT No.: PCT/JP2009/005498
§ 371 (c)(1),
(2), (4) Date: Jun. 21, 2011

(87) PCT Pub. No.: WO2010/073452
PCT Pub. Date: Jul. 1, 2010

(65) Prior Publication Data
US 2011/0257602 A1     Oct. 20, 2011

(30) Foreign Application Priority Data
Dec. 22, 2008   (JP) ................. 2008-325896

(51) Int. Cl.
*A61M 5/20*       (2006.01)
*A61M 5/145*      (2006.01)
(Continued)

(52) U.S. Cl.
CPC ................ *A61M 5/20* (2013.01); *A61J 7/0427* (2015.05); *A61J 7/0472* (2013.01);
(Continued)

(58) Field of Classification Search
CPC . A61M 5/20; A61M 5/14566; A61M 5/2066; A61M 5/2448; A61M 5/3146; A61M 5/31525; A61M 5/31546; A61M 5/347; A61M 2005/2407; A61M 2005/2488; A61M 2005/31588; A61M 2205/14; A61M 2205/3561; A61M 2205/3584; A61M 2205/50; A61M 2205/502; A61M 2205/52; A61M 2205/581; A61M 2205/582; A61M 2205/584; A61J 7/0427; A61J 7/0472
USPC ............... 604/890.1, 30, 31, 65, 67, 186, 246
See application file for complete search history.

(56) References Cited

U.S. PATENT DOCUMENTS 5,360,410 A   11/1994   Wacks
5,730,939 A    3/1998   Kurumada et al.
(Continued)

FOREIGN PATENT DOCUMENTS

CN   1505534 A   6/2004
CN   1592643 A   3/2005
(Continued)

OTHER PUBLICATIONS

International Search Report for PCT/JP2009/005498 dated Feb. 2, 2010.
Extended European Search Report for Application No. 09834269.4-1662/2361647 dated Jun. 22, 2015.

*Primary Examiner* — Theodore Stigell
*Assistant Examiner* — Lauren M Peng
(74) *Attorney, Agent, or Firm* — Pearne & Gordon LLP

(57) ABSTRACT

A medicament dispensing device capable of managing the effective use period of a medicament preparation-containing syringe by simply and accurately detecting a period of time after the start of use of the preparation. In a medicament dispensing device (1), when a medicament preparation-containing syringe (11) is replaced, a microprocessor (23) detects the time at which the replacement is performed as the time of the start of use of the preparation, and counts the elapsed time after the use of the preparation has started. Then, the microprocessor (23) notifies the result of the counting by a LCD (10), etc. to the user. Also, the microprocessor (23) detects that a syringe needle for dispensing the preparation has been mounted, and after detecting the mounting of the syringe needle, the microprocessor (23) counts the elapsed time after the start of use of the preparation. In a step S12, the microprocessor (23) checks whether or not the elapsed time counted by a timer (21) has exceeded a specified time. When an effective use period has expired, the microprocessor (23) issues a message in a step S17 that the effective period of a medicament has expired.

10 Claims, 11 Drawing Sheets

(51) Int. Cl.
*A61M 5/24* (2006.01)
*A61M 5/31* (2006.01)
*A61M 5/315* (2006.01)
*A61M 5/34* (2006.01)
*A61J 7/04* (2006.01)

(52) U.S. Cl.
CPC ......... *A61M 5/14566* (2013.01); *A61M 5/2066* (2013.01); *A61M 5/2448* (2013.01); *A61M 5/3146* (2013.01); *A61M 5/31525* (2013.01); *A61M 5/31546* (2013.01); *A61M 5/347* (2013.01); *A61M 2005/2407* (2013.01); *A61M 2005/2488* (2013.01); *A61M 2005/31588* (2013.01); *A61M 2205/14* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/584* (2013.01)

(56) References Cited

U.S. PATENT DOCUMENTS

| | | | |
|---|---|---|---|
| 6,406,460 B1* | 6/2002 | Hogan | 604/207 |
| 6,869,413 B2 | 3/2005 | Langley et al. | |
| 2001/0034506 A1 | 10/2001 | Hirschman et al. | |
| 2004/0054319 A1* | 3/2004 | Langley et al. | 604/67 |
| 2005/0209569 A1 | 9/2005 | Ishikawa | |
| 2005/0215948 A1* | 9/2005 | Adams | 604/93.01 |
| 2005/0229931 A1 | 10/2005 | Denyer et al. | |
| 2005/0277890 A1 | 12/2005 | Stewart et al. | |
| 2006/0031099 A1* | 2/2006 | Vitello et al. | 705/2 |
| 2007/0021715 A1 | 1/2007 | Kohlbrenner et al. | |
| 2007/0197968 A1* | 8/2007 | Pongpairochana et al. | 604/131 |
| 2008/0167615 A1* | 7/2008 | Niehoff | 604/131 |
| 2008/0173306 A1 | 7/2008 | Peter et al. | |
| 2009/0036771 A1* | 2/2009 | Fago et al. | 600/432 |
| 2009/0149744 A1 | 6/2009 | Nemoto et al. | |
| 2010/0238038 A1 | 9/2010 | Kohlbrenner et al. | |
| 2012/0310157 A1 | 12/2012 | Ishikawa | |

FOREIGN PATENT DOCUMENTS

| | | |
|---|---|---|
| JP | 7-501234 A | 2/1995 |
| JP | 8-262031 A | 10/1996 |
| JP | 11-076404 A | 3/1999 |
| JP | 11-276583 A | 10/1999 |
| JP | 2000-310643 A | 11/2000 |
| JP | 2003-521977 A | 7/2003 |
| JP | 4164362 B2 | 8/2008 |
| WO | 02/058767 A1 | 8/2002 |
| WO | 03/026558 A3 | 4/2003 |
| WO | 2004/004809 A1 | 1/2004 |
| WO | 2006/054651 A1 | 5/2006 |

* cited by examiner

MEDICAMENT DISPENSING DEVICE

TECHNICAL FIELD

The present invention relates to a medicine injection device equipped with a formulation syringe containing a formulation and capable of injecting the formulation into a living body and the like, and particularly, to a medicine injection device managing a term of expiration of a formulation after the start of use of the formulation.

BACKGROUND ART

When injecting medicine solution from a formulation syringe to a test subject, the operator prepares a formulation syringe containing appropriate medicine solution. A medicine injection device injects medicine solution from a formulation syringe to a test subject by moving a piston member relative to a cylinder member by means of an injecting mechanism, in response to predetermined operation.

There has been practically used a medicine injection device in which a control section calls data of a formulation from a data carrier (which is changeable by a doctor) having formulation treatment information (the number of treatment times, the expiration date of the formulation, and the medicine composition) upon injecting the formulation and which prevents the injection when it is determined that the formulation to be injected is not appropriate.

CITATION LIST

Patent Literature

PTL 1
Published Japanese Translation No. 2003-521977 of the PCT International Publication

SUMMARY OF INVENTION

Technical Problem

However, in the existing medicine injection device, there is a problem in that the term of expiration of the formulation from the start of use thereof may not be managed since the expiration date of the formulation is only the expiration date from the manufactured date thereof.

In this case, when a doctor changes a data carrier and inputs the expiration date from the start of use thereof, the formulation may be managed. However, since the data carrier is manually changed by the doctor, there is a concern that a mistake such as an omission or an erroneous input may be generated by a person.

The invention has been made in view of such circumstances, and it is therefore an object of the present invention to provide a medicine injection device capable of automatically and accurately managing a expiration date of a formulation by simply and reliably detecting a time from the start of use of a formulation syringe containing the formulation and having high safety preventing the formulation that is out of date from being injected into a body.

Solution to Problem

The medicine injection device of the present invention is equipped with a formulation syringe containing a formulation and used to inject the formulation into a living body, wherein the medicine injection device includes: a formulation replacement detecting section which detects replacement of the formulation syringe; a use start detecting section which detects the replacement of the formulation syringe as a time to start using the formulation; a use time counting section which counts a time elapsed from the start of use of the formulation; and a notification section which notifies information about the counted elapsed time.

The medicine injection device of the present invention is equipped with a formulation syringe containing a formulation and used to inject the formulation into a living body, wherein the medicine injection device includes: a formulation dissolving section which dissolves the formulation contained in the formulation syringe; a formulation dissolving detecting section which detects whether the formulation is dissolved by measuring time from the time at which the formulation starts being dissolved; a use start detecting section which detects the dissolving start time of the formulation as a time to start using the formulation; a use time counting section which counts a time elapsed from the start of use of the formulation; and a notification section which notifies information about the counted elapsed time.

Advantageous Effects of Invention

According to the invention, the expiration date from the start of use of the formulation syringe may be objectively and accurately measured by counting the time elapsed from the start of use of the formulation, and the expiration date may be easily managed.

INDUSTRIAL APPLICABILITY

The medicine injection device according to the invention may be effectively used as a medicine injection device which has a function of accurately measuring a time from the start of use of a formulation through an operation necessary for the injection of the formulation, is equipped with a formulation syringe containing the formulation, and is capable of injecting the formulation into a living body and the like. Particularly, it is useful for injection into elderly people, children and physically-challenged people by themselves, injection into patients by their families, and so forth.

DESCRIPTION OF EMBODIMENTS

Now, embodiments of the present invention will be described in detail with reference to the accompanying drawings.

Embodiment 1

Figure 1:
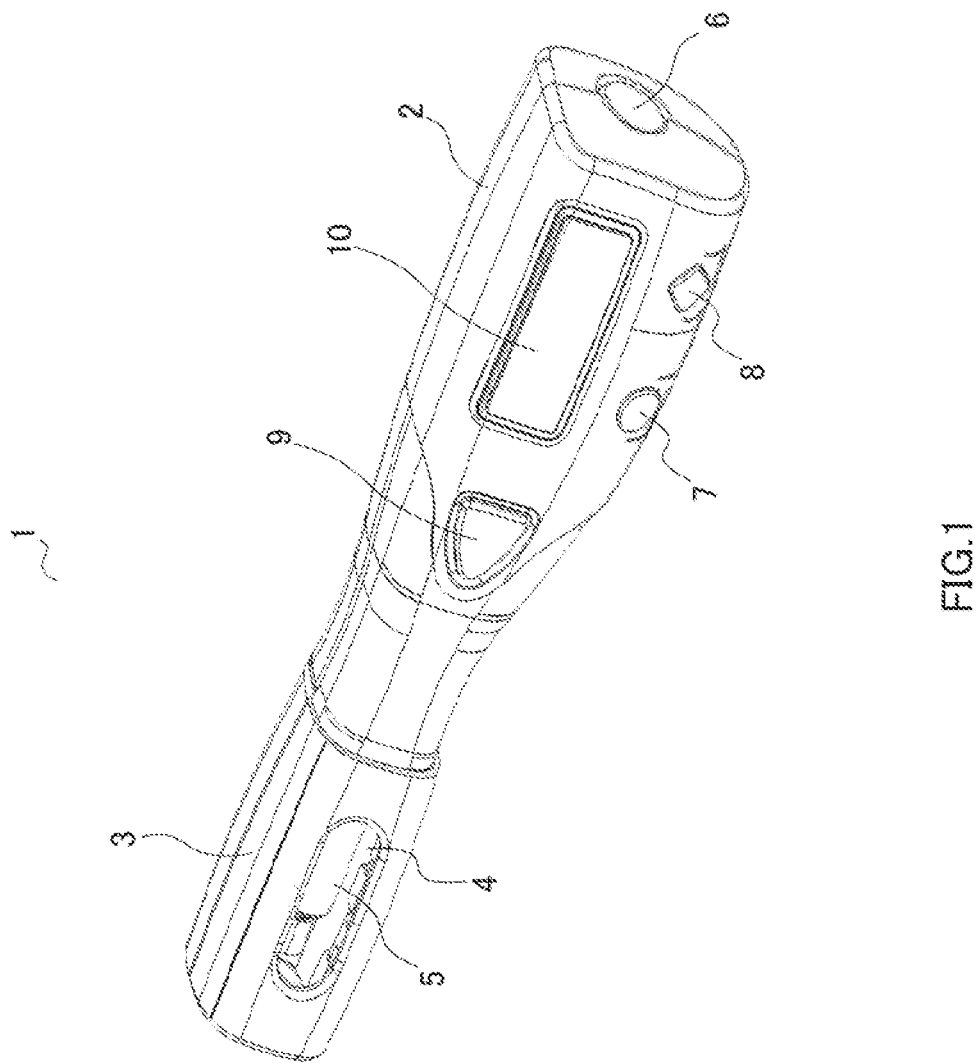
FIG. 1 is an overall perspective view showing a medicine injection device according to Embodiment 1 of the present invention.

FIG. 1 is an overall perspective view showing a medicine injection device according to Embodiment 1 of the present invention.

As shown in FIG. 1, medicine injection device 1 includes: housing 2, tip cap 3, check window 4, syringe cover 5, detecting protrusion 5b (refer to FIG. 2), power supply button 6, air-bleeding button 7, completion button 8, medicine injection button 9, and Liquid Crystal Display (LCD) 10 as a display means.

Medicine injection device 1 is covered with housing 2, which is the exterior of the apparatus body.

Tip cap 3 is attachable to or detachable from one end of housing 2 and is attached thereto or detached therefrom if necessary when formulation syringe 11 (refer to FIG. 2) is attached or detached, or an injection needle injecting a medicine solution is attached or detached.

Check window 4 is a window for checking the inside, which visually checks the presence or absence and the type of formulation syringe 11 (see FIG. 2), and the amount of formulation and so forth through syringe cover 5 made of a transparent member. Check window 4 may be formed as a transparent or semi-transparent member, or may be an opening formed cut out physically. The formation method may be arbitrarily set as long as the interior of the syringe cover may be visibly checked.

Power supply button 6 turns on and off the power supply of medicine injection device 1. Accordingly, activation for an operation of medicine injection device 1 is performed.

Figure 2:
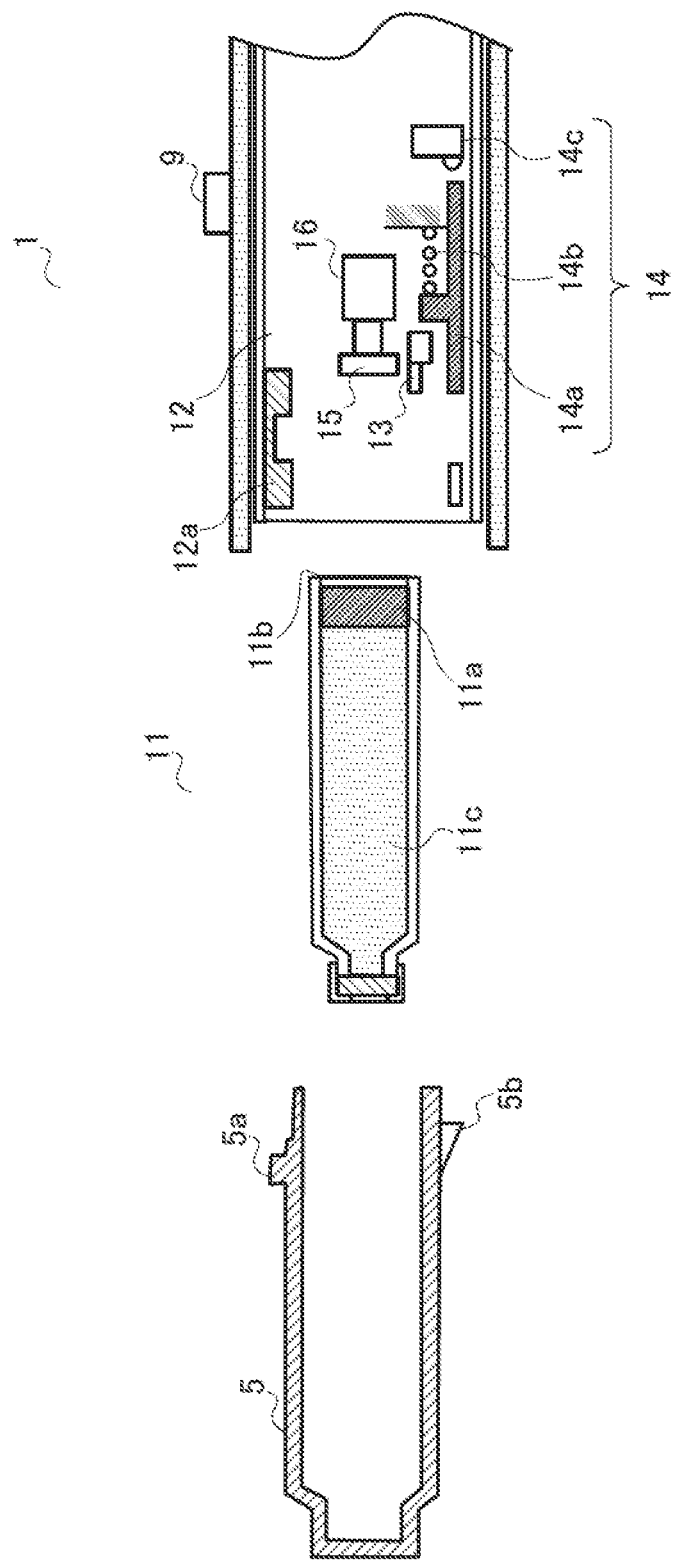
FIG. 2 is a cross sectional view showing the internal state before a formulation syringe is mounted in a syringe holder in the medicine injection device according to Embodiment 1.

Air-bleeding button 7 is used to bleed air inside formulation syringe 11 (refer to FIG. 2). Since air may be present inside formulation syringe 11 or the injection needle (a hollow needle having a cavity therein) for injection, the air present inside formulation syringe and the like is removed by air-bleeding button 7.

Completion button 8 allows the step to move the next step after air-bleeding operation, or when necessary operation, including checking various displays and so forth, is completed.

Medicine injection button 9 is pressed when injecting a formulation after the injection of the formulation is completely prepared.

LCD 10 as a display means visually displays various necessary information including a battery level, air-bleeding operation and so forth.

Further, tip cap 3 serves to cover the injection needle for the injection of the formulation so that the injection needle is not exposed. Furthermore, when the formulation is injected, skin is made contact tip cap 3 and punctured with an injection needle for formulation injection from a top opening part in tip cap 3 to inject the formulation into a body. Tip cap 3 secures safety in operation by covering a member having a sharply pointed tip such as an injection needle.

Figure 3:
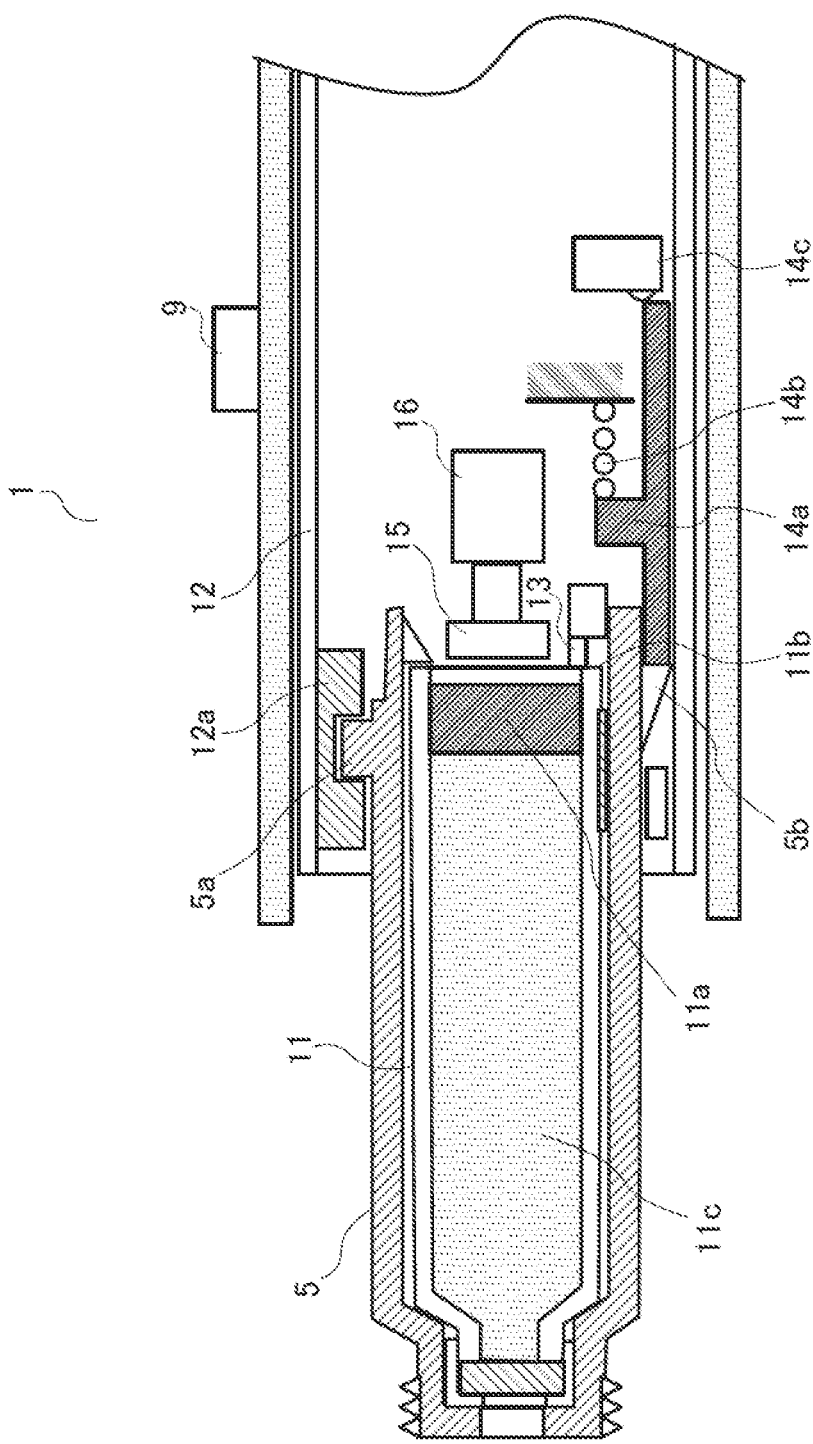
FIG. 3 is a cross sectional view showing the internal state after a formulation syringe is mounted in a syringe holder in the medicine injection device according to Embodiment 1.

FIGS. 2 and 3 are cross sectional views showing states before and after formulation syringe 11 is mounted in medicine injection device 1. FIG. 2 is an internal cross sectional view illustrating a state before formulation syringe 11 is mounted into a syringe holder which is a mounting part of medicine injection device 1, and FIG. 3 is an internal cross sectional view illustrating a state after formulation syringe 11 is mounted into the syringe holder. The syringe holder includes piston case 12, attaching and removing groove 12a, piston 15, and the like.

In a state before syringe cover 5 is mounted as shown in FIG. 2, syringe cover 5 is removed from medicine injection device 1, and, after formulation syringe 11 is inserted in medicine injection device 1, syringe cover 5 is mounted, and then fitted into piston case 12 placed in housing 2. As shown in FIG. 2, syringe cover 5 includes attaching and removing protrusion 5a and detecting protrusion 5b.

As shown in FIG. 3, in a state after syringe cover 5 is mounted in medicine injection device 1, attaching and removing protrusion 5a is fitted into attaching and removing groove 12a formed in the inner surface of piston case 12 provided in housing 2.

Detecting protrusion 5b is provided to push one end of syringe cover detecting lever 14a formed in housing 2.

Formulation syringe 11 includes seal rubber 11a and syringe end surface 11b. Seal rubber 11a is provided to preserve formulation 11c contained in the syringe by sealing formulation syringe 11.

Piston case 12 is a substantially cylindrical member provided along the inner wall surface of housing 2, where the outer peripheral surface thereof is provided with medicine injection button 9 (refer to FIG. 2) and the interior of piston case 12 is provided with piston 15, syringe detecting switch 13, syringe cover detecting section 14, and piston drive motor 16.

Medicine injection button 9 is provided on the side surface of medicine injection device 1 and is pressed when injecting formulation 11c.

Piston 15 comes into contact with seal rubber 11a provided at the rear end part of formulation syringe 11, moves forward, and presses formulation 11c toward the injection object.

Syringe detecting switch 13 is pressed down by syringe end surface 11b provided in formulation syringe 11 when syringe cover 5 equipped with formulation syringe 11 is inserted into piston case 12. Accordingly, since syringe detecting switch 13 is switched, it may be detected whether formulation syringe 11 is mounted into syringe cover 5.

Syringe cover detecting section 14 includes syringe cover detecting lever 14a, syringe cover detecting lever spring 14b, and syringe cover detection switch 14c. When syringe cover 5 is inserted into piston case 12, one end of the syringe cover detecting lever 14a is pressed by detecting protrusion 5b provided in formulation syringe 11, and the syringe cover detecting lever 14a moves against a spring force of the syringe cover detecting lever spring 14b to press down the syringe cover detection switch 14c. Accordingly, since the syringe cover detection switch 14c is switched, it may be detected whether syringe cover 5 is mounted into piston case 12. As described above, since syringe detection switch 13 detecting formulation syringe 11 and the syringe cover detecting switch 14*c* detecting the syringe cover are detected, the press operation of medicine injection button 9 becomes possible and the formulation inside formulation syringe 11 may be injected.

When piston drive motor 16 rotates in a desired direction, piston 15 moves back and forth (lengthened or shortened) in the injection direction of the formulation (the left/right direction in FIG. 3), and seal rubber 11*a* moves while being pressed by piston 15. Accordingly, a predetermined amount of the formulation inside formulation syringe is injected in accordance with the movement amount of seal rubber 11*a*.

Figure 4:
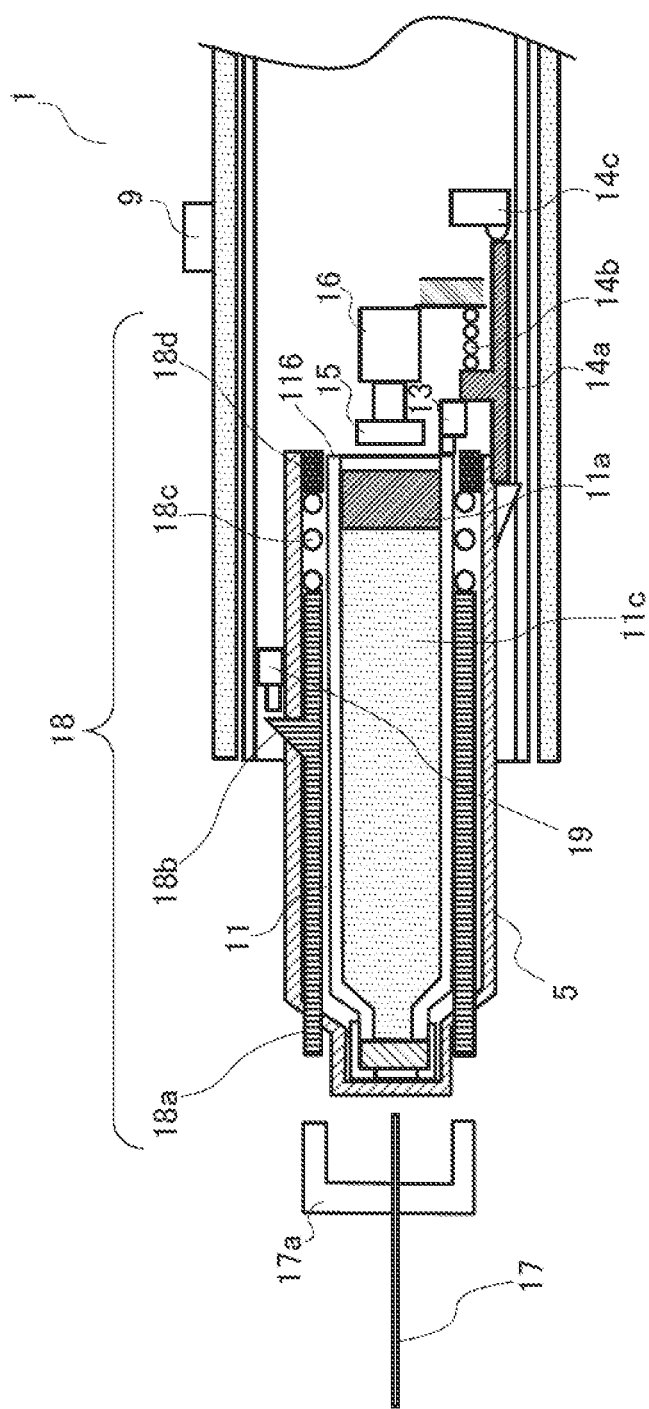
FIG. 4 is an internal cross sectional view illustrating a state before an injection needle of the medicine injection device according to Embodiment 1 is mounted on a syringe cover.
Figure 5:
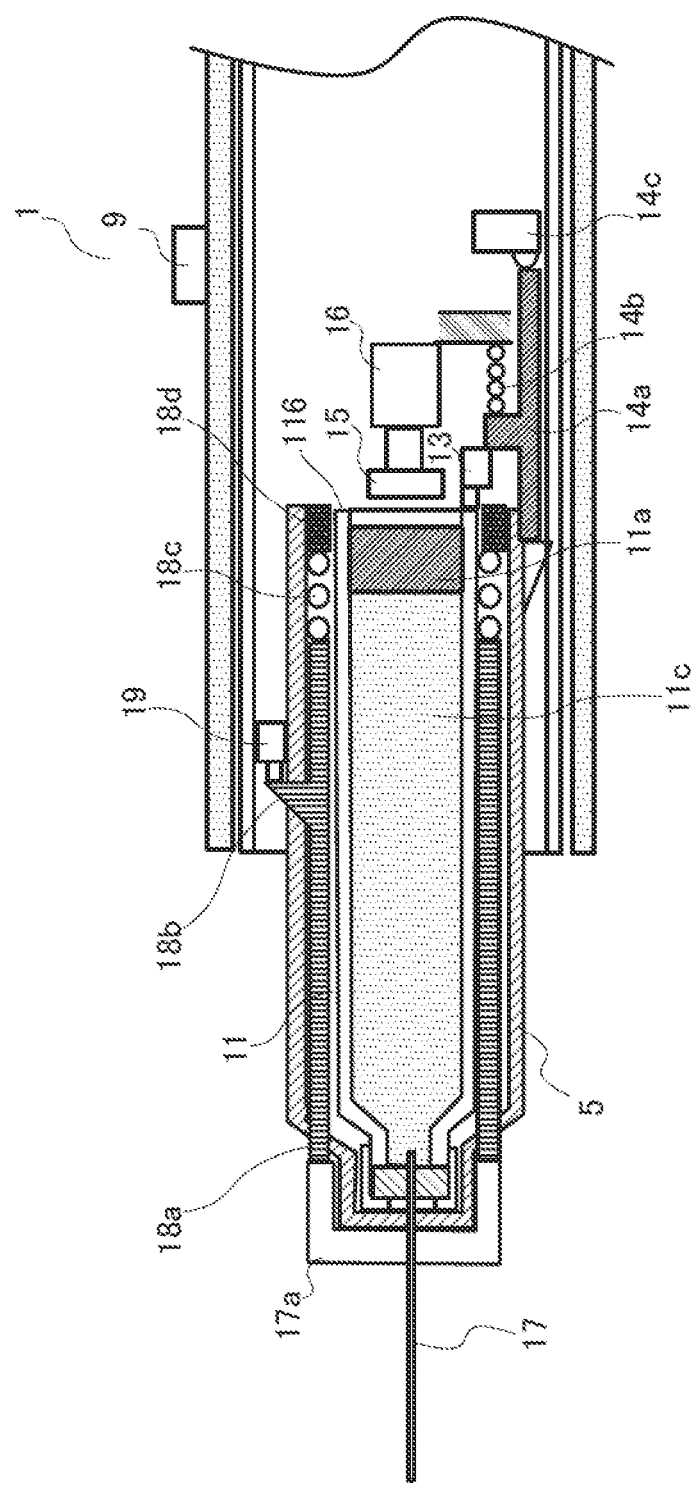
FIG. 5 is an internal cross sectional view illustrating a state after the injection needle of the medicine injection device according to Embodiment 1 is mounted on the syringe cover.

FIGS. 4 and 5 are internal cross sectional views respectively illustrating the states before and after injection needle 17 is mounted on syringe cover 5. FIG. 4 is an internal cross sectional view illustrating a state before injection needle 17 is mounted on syringe cover 5, and FIG. 5 is an internal cross sectional view illustrating a state after injection needle 17 is mounted on syringe cover 5.

As shown in FIG. 4, syringe cover 5 is provided with injection needle detecting lever mechanism 18, and the interior of medicine injection device 1 is provided with the injection needle detecting switch 19. Injection needle detecting lever mechanism 18 and injection needle detecting switch 19 constitute an injection needle detecting means to detect the injection needle.

Injection needle detecting lever mechanism 18 provided in syringe cover 5 includes injection needle detecting lever 18*a*, detecting protrusion 18*b*, injection needle detecting lever spring 18*c*, and spring fixation lid 18*d*.

As shown in FIG. 5, in the injection needle detecting lever mechanism 18, when injection needle 17 is attached to the front end of syringe 5, injection needle detecting lever 18*a* is pressed by one end of injection needle holding part 17*a*, and injection needle detecting lever 18*a* moves against a spring force of the injection needle detecting lever spring 18*c* so that detecting protrusion 18*b* moves. Accordingly, injection needle detecting switch 19 provided inside medicine injection device 1 is pressed down by detecting protrusion 18*b*, thereby detecting whether injection needle 17 is attached to syringe cover 5.

Figure 6:
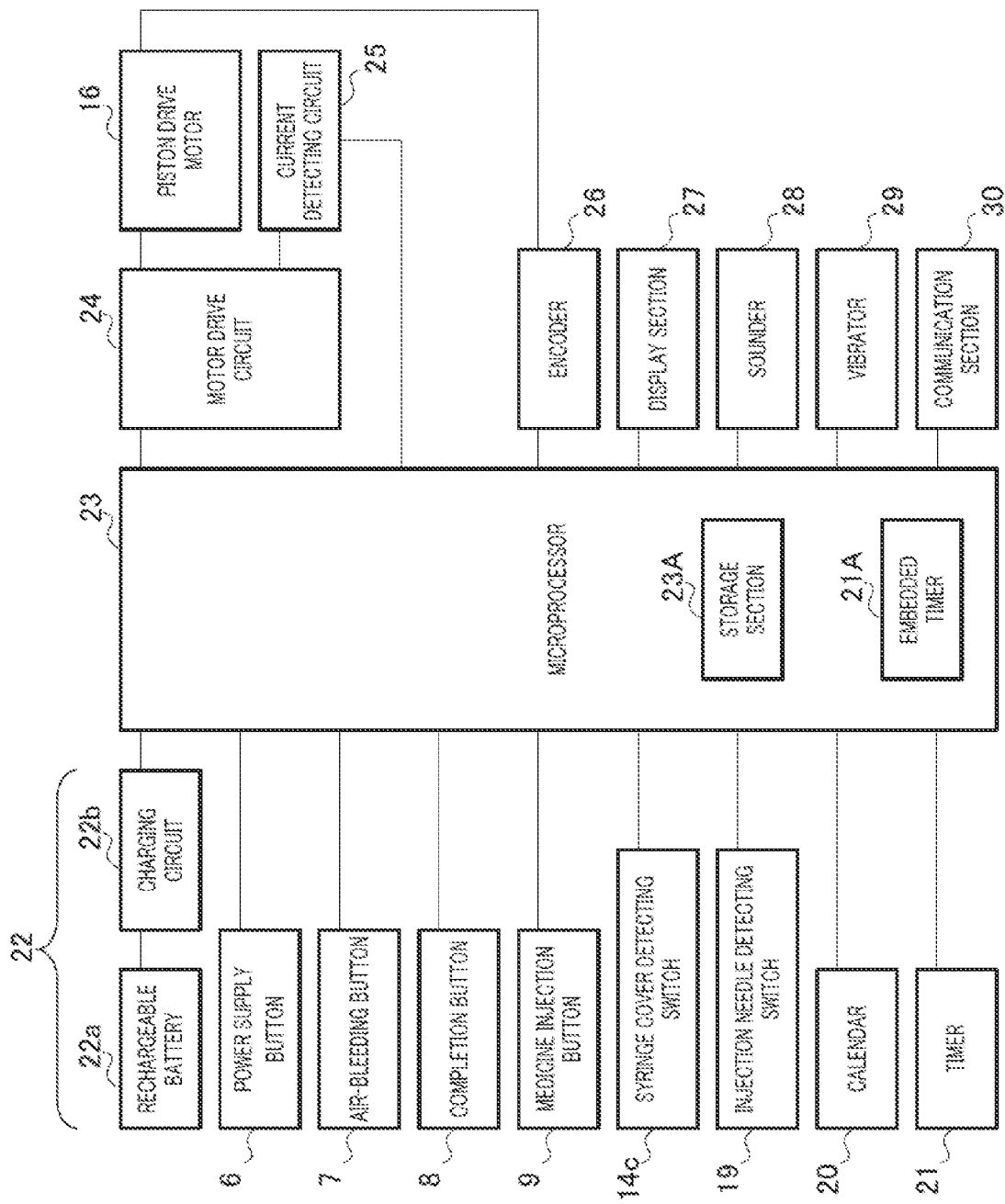
FIG. 6 is a block diagram showing the electrical circuit of the medicine injection device according to Embodiment 1.

FIG. 6 is a block diagram showing the electrical circuit of medicine injection device 1 and its nearby parts.

As shown in FIG. 6, medicine injection device 1 includes: power supply button 6, air-bleeding button 7, completion button 8, medicine injection button 9, syringe cover detecting switch 14*c*, injection needle detecting switch 19, calendar 20, timer 21, power supply section 22 as a power supply of the medicine injection device, microprocessor 23, piston drive motor 16, motor drive circuit 24, current detecting circuit 25, encoder 26, display section 27 (LCD 10), sounder 28, vibrator 29, and communication section 30.

Each of power supply button 6, air-bleeding button 7, completion button 8, medicine injection button 9, syringe cover detecting switch 14*c*, piston drive motor 16, and injection needle detecting switch 19 is electrically connected to microprocessor 23 as a control section.

Power supply button 6 is used to switch the power supply between on and off in medicine injection device 1. By turning on the power supply, medicine injection device 1 is activated.

Air-bleeding button 7 is used to perform air-bleeding operation, which is generally performed as advance preparation before medicine injection.

Completion button 8 is pressed at the time necessary operation is completed to move the step to the next step.

Medicine injection button 9 is used when the medicine injection operation is needed.

Microprocessor 23 controls the overall operation of the apparatus and also controls operation of the apparatus corresponding to each of various buttons 6 to 9, according to electrical signals transmitted from these buttons 6 to 9. Further, microprocessor 23 includes storage section 23A and embedded timer 21A.

Storage section 23A includes a ROM, a RAM and a semiconductor memory such as an electrically erasable programmable ROM (EEPROM) or a flash memory, and stores data of the expiration date of the formulation. The ROM stores in advance a software program executed by microprocessor 23 or fixed data. The RAM is used as a so-called working memory which temporarily stores data related to the injection time and the injection amount, use time count data, data used for calculation, and a calculation result. The RAM stores data related to the expiration date of the predetermined formulation even when power supply button 6 is turned off since the EEPROM stores a part or all of the data for power backup.

Embedded timer 21A has a timekeeping function.

In particular, microprocessor 23 controls a formulation injection operation. Specifically, when medicine injection button 9 is pressed, microprocessor 23 checks syringe cover detecting switch 14*c* and injection needle detecting switch 19 to confirm whether formulation syringe 11 is normally mounted. After it is confirmed that formulation syringe 11 is normally mounted, microprocessor operates piston drive motor 16 by transmitting an electrical signal to motor drive circuit 24. When piston drive motor 16 rotates, piston 15 (refer to FIG. 2) mechanically connected to piston drive motor 16 moves forward so that the formulation inside formulation syringe 11 is administrated into a body. The injection amount of the formulation is determined and managed by counting an output signal (a pulse signal) from encoder 26 connected to piston drive motor 16.

Further, microprocessor 23 also functions as a use time counting means to count the time elapsed from the start of use of the formulation by executing a program described later in FIGS. 7 and 8. Furthermore, microprocessor 23 may inject a predetermined amount of the formulation into a body by automatically controlling the motor drive circuit based on the information of the predetermined formulation injection amount. That is, microprocessor 23 also has a medicine dosage control section. In addition, microprocessor 23 further has a medicine injection information setting section that sets information about medicine injection such as the dosage of medicine. Further, the formulation injection information such as the formulation injection amount is stored in the memory.

Calendar 20, timer 21, and embedded timer 21A inside microprocessor 23 are used for the management of time of medicine injection device 1. For example, when the formulation is injected, a user may effectively manage the time by referring to a current time displayed on LCD 10 during the injection.

Calendar 20 is used to manage and monitor a comparatively long time such as a day, and timer 21 or embedded timer 21A is used to manage and monitor a comparatively short time such as an hour and a minute. Of course, calendar 20, timer 21, and embedded timer 21A may be independently used, any one of timer 21 and embedded timer 21A may be provided. Further, when a plurality of them are simultaneously used and compared with each other to monitor each other and correct a difference in time, the reliability in the management of time may be improved.

Power supply section 22 represents the power supply part of medicine injection device 1. Power supply section 22 has a mobility-focused configuration and is composed of rechargeable battery 22*a* and charging circuit 22*b*. Nickel metal hydride battery and a lithium-ion battery may be used as rechargeable battery. Here, power supply section 22 can operate using a primary battery.

Since a current larger than that of a normal case flows when an abnormal load is applied to piston drive motor 16, current detecting circuit 25 detects the current in the abnormal case and transmits an electrical signal to microprocessor 23. When microprocessor 23 receives the electrical signal, microprocessor determines that it is an abnormal state, stops the medicine injection operation, and informs the user of the abnormality by displaying an error or the like on LCD 10, allowing the display LED to flicker, outputting a warning sound from sounder 28, or generating a vibration using vibrator 29.

Each of display section 27, sounder 28, and vibrator 29 is used as a notification means with respect to the user. Display section 27 indicates LCD 10 as a display means or an LED and an organic EL shown in FIG. 1, and is used to visually check the current operation state, the display of warning, or the like.

An optical reporting method using a display LED and so forth can be realized by illuminating, flashing and so forth. In addition, when a multicolor type display LED and so forth is used, it is possible to visually report the degree of importance or urgency of the reported content by switching RGB components and illuminating or flashing any color based on the ratio between colors. Therefore, it is useful for people with impaired hearing.

Further, the display LED may be provided separately from LCD 10.

Display section 27 may be arranged nearby a mounting section to mount formulation syringe 11 in medicine injection device 1.

Sounder 28 outputs a warning sound, a sound representing the medicine injection operation, and a sound representing a battery charging start and end. Further, sounder 28 includes therein a voice synthesis LSI (not shown) and performs a voice announcement explaining the operation or the like. Accordingly, the medicine injection device may be effectively used for a person with impaired vision.

Vibrator 29 informs the user of warning or the like by the vibration of medicine injection device 1. Since vibrator 29 vibrates instead of the voice announcement or together with the voice announcement, the vibrator may inform the user of the abnormality or the like so that the operation state of medicine injection device 1 or the like may be effectively informed.

Communication section 30 communicates with other devices (for example, a PC and the like) in a wired or wireless manner. For example, examples of communication section 30 may include universal serial bus (USB), infrared communication, Bluetooth (trademark), wired and wireless LAN, radio frequency (RF) communication, a local area wireless communication, and the like. In the embodiment, communication section 30 is used as an input means which inputs data of expiration date of the formulation. Furthermore, the input section may be a key operation means (not shown).

Communication section 30 is used when the expiration date needs to be changed via a wireless communication or a wired communication. Specifically, communication section 30 uses an infrared communication, an RF communication, or the like in the case of the wireless communication and uses a PC or a keyboard via a USB, a LAN, or the like in the case of the wired communication to set and change the formulation injection data, the formulation expiration date data, or the like. In the case of using a PC, communication section 30 receives time-related data stored in advance on the memory of the PC and stores the time-related data on storage section 23A of microprocessor 23. Further, communication section 30 may store the numerical value data directly input via the keyboard of the PC or the like on storage section 23A. Then, the communication section stores the data in its internal memory to set, change, and update the data.

Now, operation of medicine injection device 1 configured as described above, will be explained.

First, an operation of detecting the time of the start of use will be described.

Figure 7:
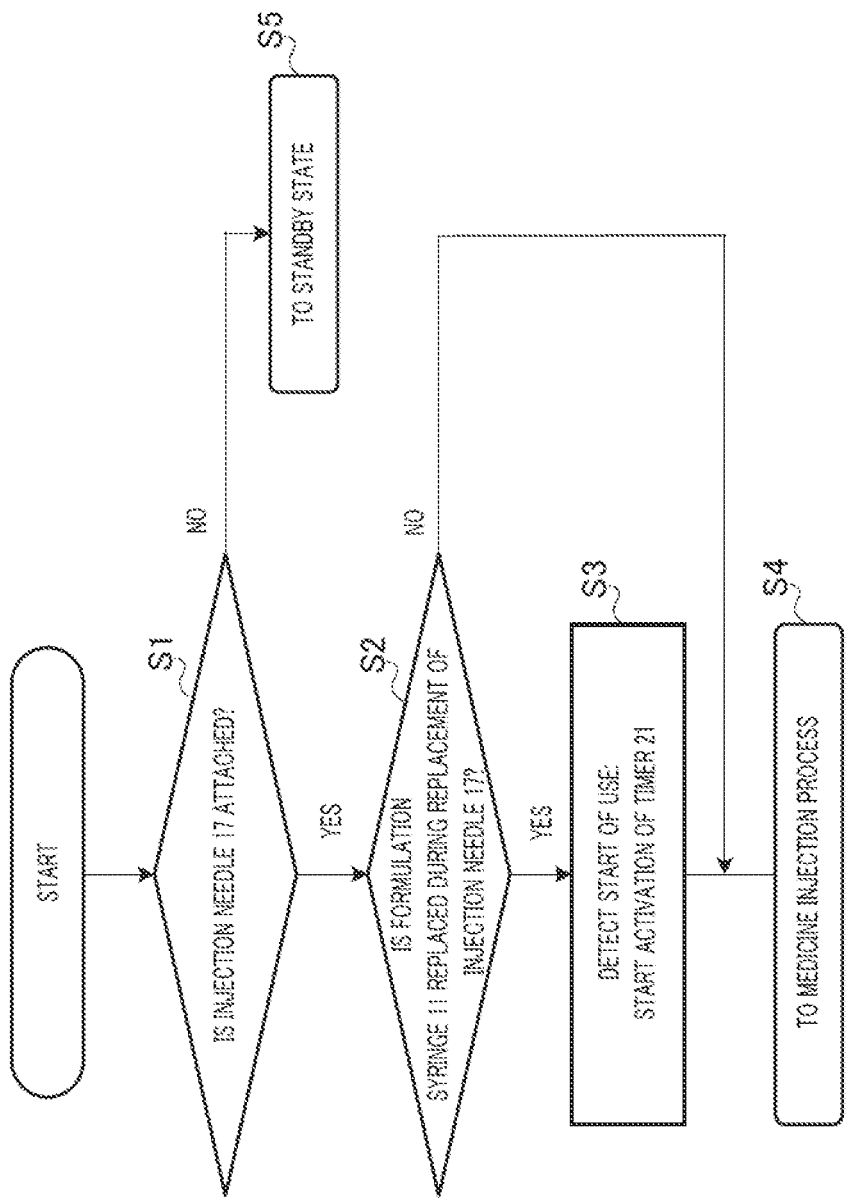
FIG. 7 is a flowchart illustrating an operation of detecting a time of the start of use of the medicine injection device according to Embodiment 1.

FIG. 7 is a flowchart illustrating the operation of detecting the time of the start of use of medicine injection device 1, and the operation is executed by microprocessor 23. In the figure, S represents each step in the operation flow.

In step S1, microprocessor 23 checks whether injection needle 17 is correctly mounted on syringe cover 5 by using injection needle detecting switch 19 and the like. When injection needle 17 is correctly mounted, step S2 is performed. When injection needle 17 is not mounted, the standby state of step S5 is performed.

In step S2, microprocessor 23 checks whether formulation syringe 11 is replaced during a time from the precedent attachment of injection needle 17 to the current attachment of the injection needle. When formulation syringe 11 is not replaced, step S4 is performed and the medicine injection process is performed.

When formulation syringe 11 is replaced, in step S3, microprocessor 23 starts the timekeeping of timer 21, and counts a time elapsed from the start of use of formulation syringe 11 by setting the replace time of the formulation syringe as the use start time.

In step S4, the process of the flowchart ends and the medicine injection process is performed.

Figure 8:
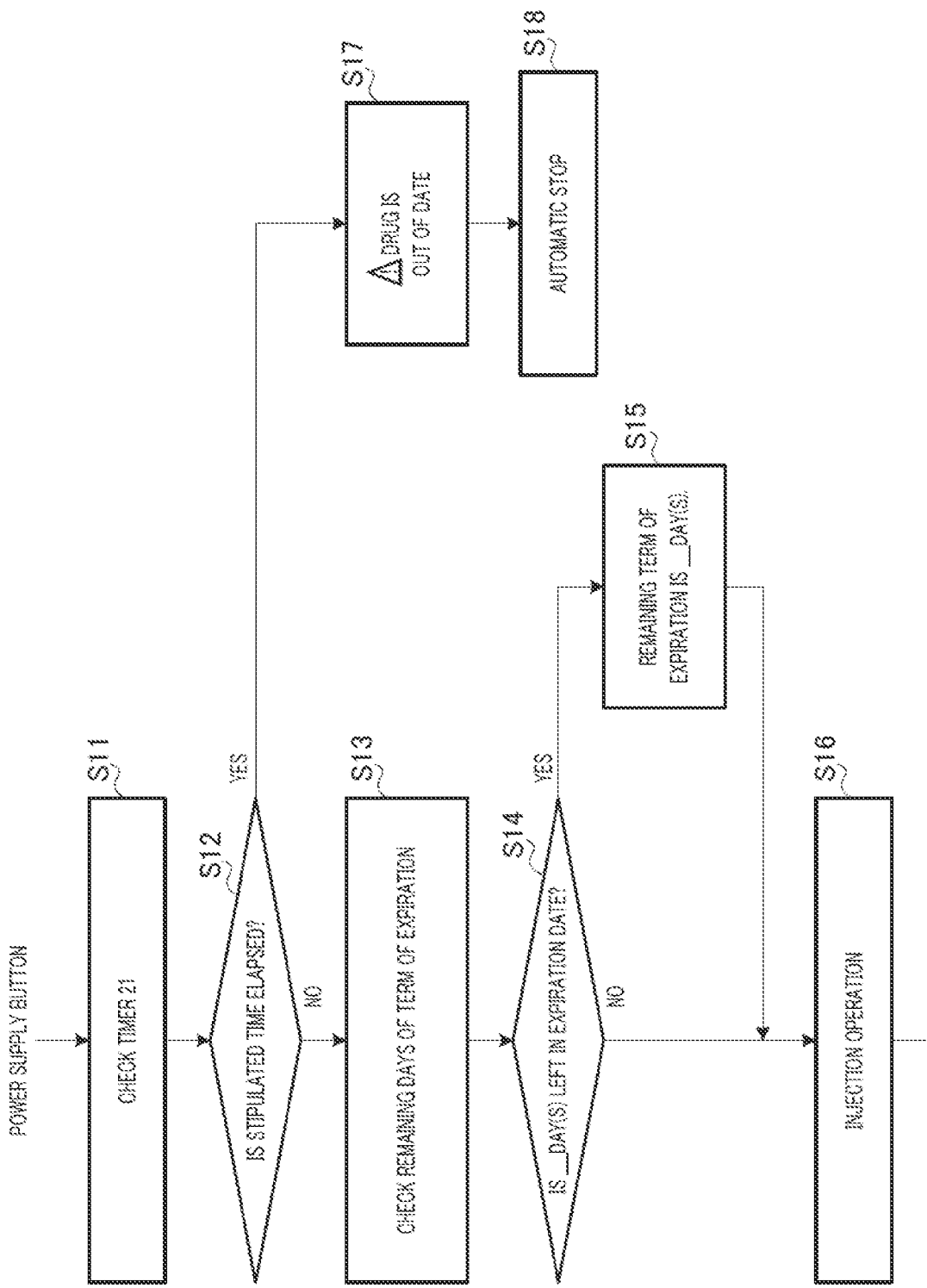
FIG. 8 is a flowchart determining an expiration date of the medicine injection device according to Embodiment 1.

FIG. 8 is a flowchart determining the expiration date of medicine injection device 1, and the process is executed by microprocessor 23. This flow is started when power supply button 6 is pressed.

In step S11, microprocessor 23 checks the time elapsed from the time of the start of use of the formulation using timer 21.

In step S12, microprocessor 23 checks whether the elapsed time of timer 21 is elapsed by a stipulated time. Here, the stipulated time indicates the term of expiration of the formulation.

When the term of expiration is over, microprocessor 23 determines that the term of expiration of the formulation is over and performs the process of step S17.

In step S17, microprocessor 23 generates a warning message that the expiration date of the medicine is over. Specifically, in order to inform the user that the expiration date is over, microprocessor 23 displays a warning message of "! medicine is out of date" on LCD 10 as a display means so that the user is informed that the expiration date of the medicine is over. Further, microprocessor 23 performs a process of generating a warning sound using sounder 28 or generating a vibration using vibrator 29. In addition, reporting may be made by flashing a display LED. Moreover, combination of these is possible.

In this manner, since the user is reliably informed that the expiration date of the formulation is over when the term of expiration of the formulation is over, the user may reliably recognize the possibility that the formulation that is out of date may not be safely used due to oxidization thereof or the like. Accordingly, the user may safely use the medicine injection device.

In step S18, microprocessor 23 automatically stops the operation of medicine injection device 1 so that the formulation may not be injected any more. The reason the formulation is prohibited from being injected into the user when the expiration date of the formulation is over is because the formulation that is out of date may have an adverse influence on a human body due to oxidization thereof or the like and may not be safely used. The configuration in which medicine injection device 1 automatically prohibits the injection of the formulation is very effective from the viewpoint of the user's safety.

In step S12, the expiration date of the formulation is within the stipulated time, step S13 is performed.

In step S13, microprocessor 23 calculates the number of remaining days until the expiration date of the formulation from the elapsed time of timer 21.

In step S14, microprocessor 23 checks whether or not the calculated number of days matches a predetermined number of days (for example, two days) before the expiration date.

When the number of remaining days matches certain number of days, in step S15, microprocessor 23 displays the number of days until the expiration date of the medicine on LCD 10 as a display means. Since the remaining days until the expiration date of the formulation are displayed on LCD 10 as a display means or the like, the user may simply check the remaining days with naked eyes. Further, the remaining time until the expiration date of the formulation may be output by a voice using sounder 28 or the like or be output by the generation of vibration. Alternatively, these methods may be combined with each other. When voice output or vibration is used, the user and, of course, the person with impaired vision may easily check the remaining days. Further, since the remaining days are output by vibration, even the person with impaired vision may easily check the remaining days without giving a trouble to the peripheral persons.

In this manner, when the remaining time reaches a predetermined threshold value before the expiration date (for example, when two days are left), the notification means may reliably inform the user that the expiration date will be expired through an alarm or the like. Accordingly, the user may prepare a formulation syringe for replace with enough time.

In step S14, when the calculated number of remaining days does not match a predetermined number of days until the expiration date or after the number of remaining days is displayed in above step S15, the step moves onto step S16. That is, when there is still enough time until the expiration date of formulation syringe 11, it is determined that the formulation syringe is correctly mounted without the warning or the display of the remaining term of expiration, and the formulation injection operation of step S16 is performed.

Figures 9, 10:
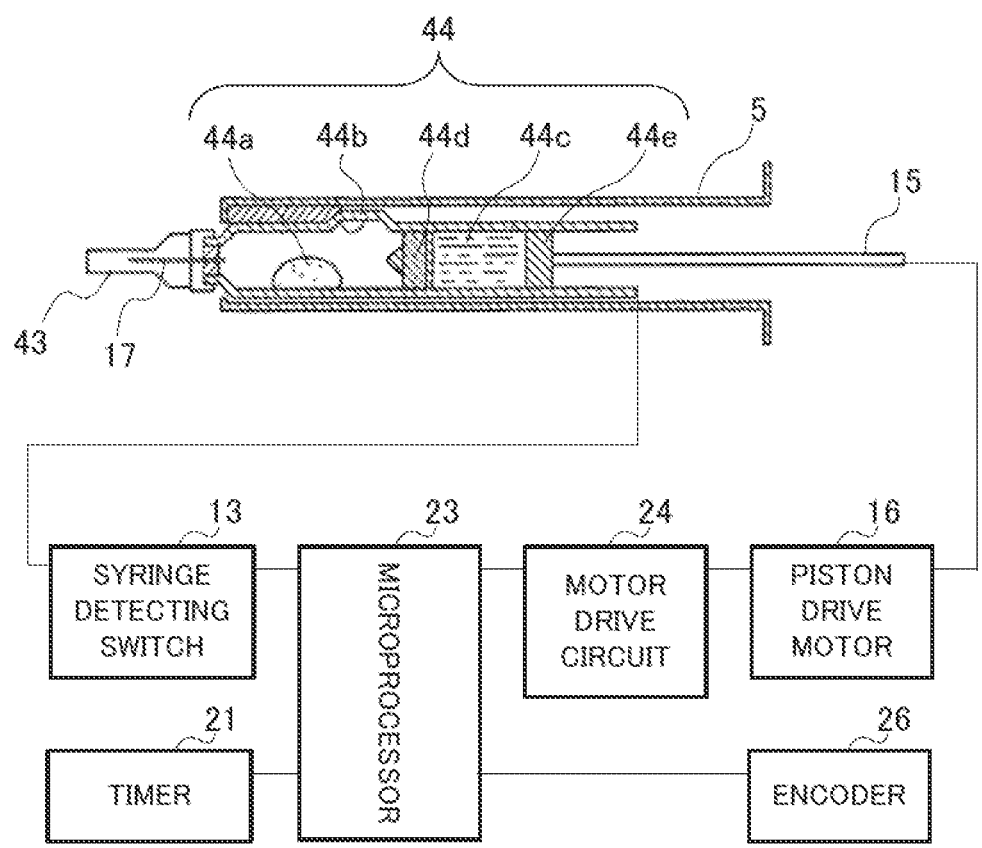
FIG. 9 is a diagram illustrating a display example of an LCD of the medicine injection device according to Embodiment 1.
FIG. 10 is an internal cross-sectional view illustrating a medicine injection device automatically dissolving a formulation according to Embodiment 2 of the invention.

FIG. 9 is a diagram illustrating a display example of LCD 10 as a display means of the medicine injection device.

The example of FIG. 9 indicates, for example, a display example of step S15 of FIG. 8. The message of step S17 of FIG. 8 may be displayed in the same manner. FIG. 9(*a*) illustrates a progress bar type. In this display method, the current elapsed time may be intuitively recognized by the graphical display. FIG. 9(*b*) illustrates a type displaying the use days. The term of expiration may be accurately recognized by displaying the specific date.

As described above in detail, in medicine injection device 1 of the embodiment, microprocessor 23 detects the replace time of formulation syringe 11 as the time to start using the formulation, and counts the elapsed time from the start of use of the formulation. Then, since microprocessor 23 informs the user of the counted result by displaying the result on LCD 10 as a display means or the like, the time elapsed from the start of use of formulation syringe 11 may be simply and reliably detected and the term of expiration may be managed.

Accordingly, the user may not perform an operation of recording the term of expiration from the start of use by himself or herself, and easily manage the counted elapsed time from the start of use without any trouble. Since the setting (when changing the data carrier) using the manual input is not needed, a mistake such as an omission or an erroneous input generated by a person may be prevented, and the formulation that is out of date may be prevented from being injected into a body by mistake, thereby providing the medicine injection device with high safety.

Further, in the embodiment, since the formulation syringe detecting means shown in FIGS. 2 and 3 and the injection needle detecting means shown in FIGS. 4 and 5 are provided, the time to start using the formulation is detected. That is, the replacement of the formulation syringe and the attachment of the injection needle are operations necessary for the injection of the formulation, and the medicine injection device automatically detects the start of use of the formulation during the necessary operations. Specifically, the attachment of the injection needle for the injection of the formulation is detected, and after the attachment of the injection needle is detected, the elapsed time from the start of use of the formulation is counted. Accordingly, the elapsed time from the start of use of the formulation may be more reliably and simply managed, and the user may be easily informed of the replace timing of the formulation by a warning.

Embodiment 2

FIG. 10 is an internal cross sectional view illustrating a medicine injection device automatically dissolving a formulation according to Embodiment 2 of the invention. The same symbols will be given to the same components as those of FIG. 6 and the same point will not be repeated.

In Embodiment 2, there is shown a formulation use start detecting means when formulation syringe 44 dissolved in use is used.

As shown in FIG. 10, formulation syringe 44 is of a mixture use type in which two or more formulations are mixed with each other in advance before the formulation is injected into a body and are used in a mixed state, and includes powdered formulation 44*a*, syringe convex part 44*b*, medicine solution 44*c*, rubber A44*d*, and rubber B44*e*. Furthermore, protection cap 43 is attached to injection needle 17 mounted on formulation syringe 44.

In formulation syringe 44 dissolved in use, the term of expiration after dissolving the formulation is set. Further, medicine injection device 1 may automatically or semi-automatically dissolve powdered formulation 44*a* and medicine solution 44*c*. Accordingly, medicine injection device 1 may manage the term of expiration by starting timer 21 (which may be embedded timer 21A of microprocessor 23) while the formulation dissolving time is set as the use start time.

When formulation syringe 44 is attached to medicine injection device 1, the attachment of formulation syringe 44 is detected by syringe detecting switch 13, and a detection electrical signal is transmitted to microprocessor 23.

Microprocessor 23 rotates piston drive motor 16 by transmitting the electrical signal to motor drive circuit 24 and moves piston 15 mechanically connected thereto forward. Microprocessor 23 dissolves powdered formulation 44*a* and medicine solution 44*c* inside formulation syringe 44 by moving piston 15 forward by a predetermined amount. When piston 15 moves forward (the left direction of FIG. 10), rubber B44*e* moves forward (the left direction of FIG. 10), and rubber A44*d* and medicine solution 44*c* also move forward (the left direction of FIG. 10) by the forward movement. At this time, when a part of medicine solution 44c starts to enter syringe convex part 44b having a slightly larger inner diameter of the syringe, medicine solution 44c flows toward powdered formulation 44a to bypass rubber A44d via syringe convex part 44b and is mixed with powdered formulation 44a. The distance moving piston 15 forward may be obtained by counting the number of pulses generated from encoder 26 connected to piston drive motor 16. Further, microprocessor 23 may determine whether powdered formulation 44a is dissolved by medicine solution 44c by counting the number of predetermined pulses.

Figure 11:
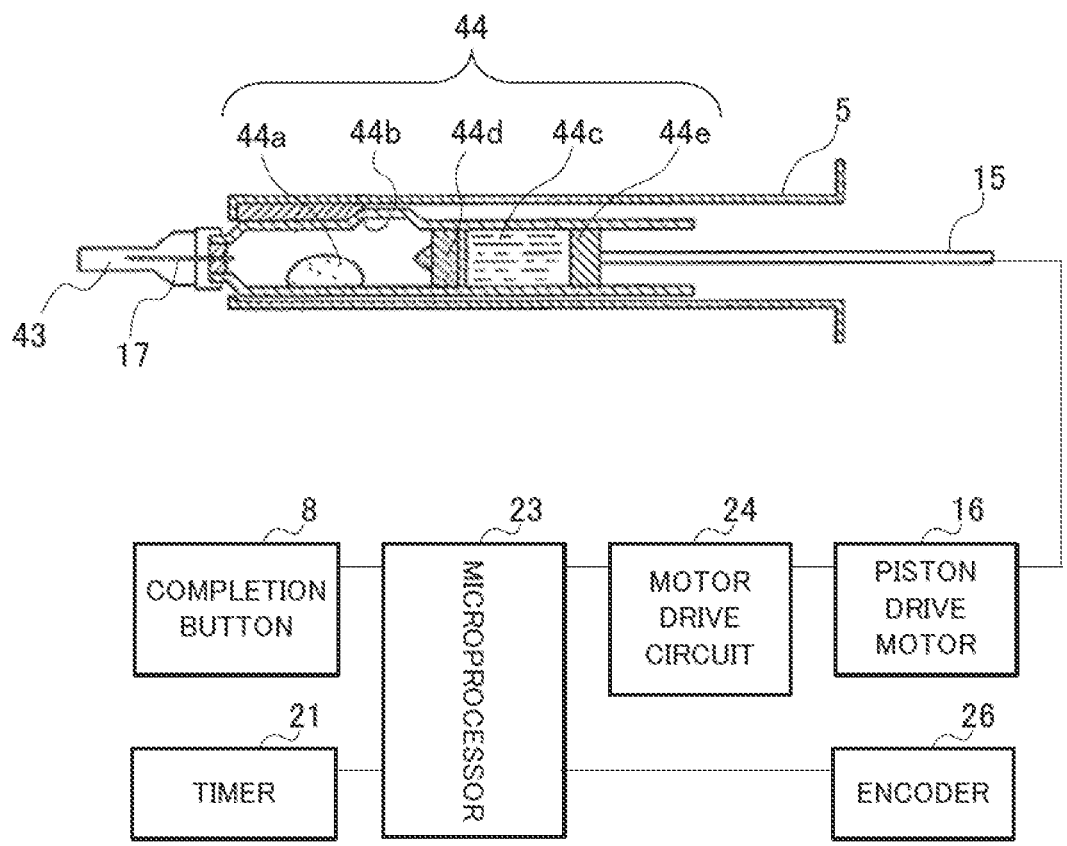
FIG. 11 is an internal cross-sectional view illustrating the medicine injection device semi-automatically dissolving the formulation according to Embodiment 2.

FIG. 11 is an internal cross sectional view illustrating the medicine injection device semi-automatically dissolving the formulation. The same symbols will be given to the same components as those of FIG. 10.

FIG. 11, the replace of formulation syringe 44 is determined based on whether completion button 8 is pressed down instead of the detection using syringe detecting switch 13 of FIG. 10. When completion button 8 is pressed, powdered formulation 44a and medicine solution 44c are made to be dissolved and timer 21 is activated. This may be applied to a medicine injection device or the like using a disposable automatic dissolving medicine.

In this manner, according to Embodiment 2, since the formulation dissolving means to dissolve the formulation inside formulation syringe 44 and the formulation dissolving detecting section detecting the dissolved state of the formulation are provided, when powdered formulation 44a inside formulation syringe 44 is dissolved in use, the dissolved state of the formulation may be easily detected, and the elapsed time from the start of use may be counted by starting timer 21 while the formulation dissolving time is set as the use start time in the use time count section. Further, the formulation syringe has a formulation used by dissolving powdered formulation 44a in different medicine solution 44c. In this case, the expiration date is decided after the dissolving of powdered formulation 44a. Accordingly, the elapsed time after the dissolving may be effectively detected when using the dissolving type (mixture use type) formulation syringe.

Further, in Embodiment 2, in formulation syringe 44 using powdered formulation 44a while being dissolved in medicine solution 44c, the start of use is detected by detecting the dissolving of the formulation. The dissolving of the formulation is an operation necessary for the injection of the formulation, and the medicine injection device automatically detects the time to start using the formulation (here, the powdered formulation dissolving timing) during the necessary operation. Accordingly, it is found that the elapsed time from the start of use of the formulation may be reliably and simply managed and the user may be easily informed of the replace timing of the formulation.

Embodiment 3

In Embodiment 3, the needle attachment detection function is not provided, and the activation of timer 21 when medicine injection button 9 is pressed will be described in detail, where the medicine injection button is configured to be pressed down upon injecting the formulation.

Figure 12:
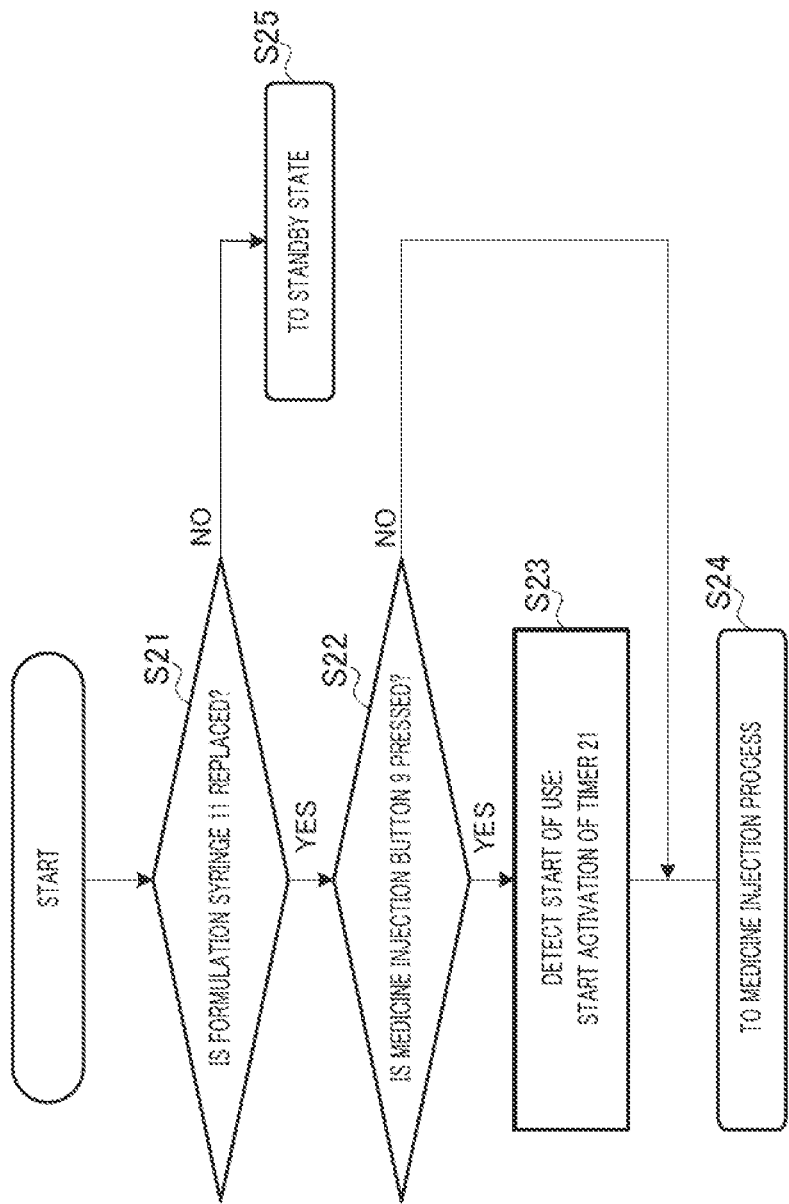
FIG. 12 is a flowchart illustrating an operation of detecting a time of the start of use of a medicine injection device without a function of detecting an injection needle mounted state according to Embodiment 3 of the invention.

FIG. 12 is a flowchart illustrating an operation of detecting a time of the start of use of a medicine injection device without a function of detecting an injection needle mounted state according to Embodiment 3 of the invention.

In Embodiment 1, timer 21 is activated by two types of detections, that is, the detection of the replace of formulation syringe 11 and the detection of the attachment of injection needle 17, and the term of expiration is checked. In Embodiment 3, the detection of the attachment of the injection needle is not provided, but the detection may realized by the medicine injection operation.

First, in step S21, microprocessor 23 determines whether formulation syringe 11 is replaced. For example, this is detected by the method shown in FIGS. 2 and 3. It is assumed that the disposable medicine injection device is not used yet. Microprocessor 23 determines that it is new formulation syringe 11 when formulation syringe 11 is replaced. When formulation syringe 11 is in use, the standby state of step S25 is performed.

In step S22, microprocessor 23 determines whether medicine injection button 9 is pressed down. When it is determined as new formulation syringe 11 and medicine injection button 9 is pressed down, microprocessor 23 determines that it is the use start timing of formulation syringe 11, and in step S23, timer 21 is activated. When medicine injection button 9 is not pressed down, step S24 is directly performed.

In step S24, the process of the flowchart ends and the medicine injection process is performed.

The reason the injection needle attachment detection function is not provided is because the medicine injection device needs to be further decreased in size.

Further, as a notification means, the display of characters on LCD 10 as a display section is used. In addition to this method, sounder 28 (refer to FIG. 4) may generate a voice output of "the expiration date of the formulation is over. Please replace a new product" or "two days are left until the expiration date of the formulation. Please prepare a new formulation." Accordingly, even a person with impaired vision may safely use the formulation.

Further, since vibrator 29 is provided, a warning is generated by vibration. Accordingly, even a person with impaired vision may more safely use the medicine injection device.

In this manner, according to Embodiment 3, the start of use of the formulation may be detected based on an operation of pressing medicine injection button 9 instead of the formulation syringe detecting means shown in FIGS. 2 and 3 and the injection needle detecting means shown in FIGS. 4 and 5. The replacement of the formulation syringe and the pressing of the button for the injection of the formulation are operations necessary for the injection of the formulation, and the start of use of the formulation is automatically detected during the necessary operations. Accordingly, the elapsed time from the start of use of the formulation may be more reliably and simply managed, and the user may be easily informed of the replace timing of the formulation by a warning.

Further, since the injection needle detection function shown in FIGS. 4 and 5 is not provided, the medicine injection device may be further decreased in size.

The above description is illustration of preferred embodiments of the present invention and the scope of the invention is not limited to this.

For example, in the above-described embodiments, the laser emission device or the needle medicine injection device is used as the puncturing means, the invention is not limited thereto, and both may be simultaneously used as the puncturing means.

Although the name "medicine injection device" is used in the embodiments for ease of explanation, "medicine injecting device", "medicine injection system" and so forth are possible naturally.

Moreover, the type, the number, the connection method and so forth of components constituting the above-described medicine injection device are not limited.

The above-described medicine injection method may be realized by a program to operate this medicine injection method. This program is stored in a computer-readable storage medium.

The disclosure of Japanese Patent Application No. 2008-325896, filed on Dec. 22, 2008, including the specification, drawings and abstract, is incorporated herein by reference in its entirety.

REFERENCE SIGNS LIST

1 Medicine injection device
2 Housing
3 Tip cap
4 Check window
5 Syringe cover
5b Detecting protrusion
6 Power supply button
7 Air-bleeding button
8 Completion button
9 Medicine injection button
10 LCD
11, 44 Formulation syringe
11a Seal rubber
11b Syringe end surface
11c Formulation
12 Piston case
13 Syringe detecting switch
14 Syringe cover detecting section
14a Syringe cover detecting lever
14b Syringe cover detecting lever spring
14c Syringe cover detecting switch
15 Piston
16 Piston driving motor
17 Injection needle
18 Injection needle detecting lever mechanism
18a Injection needle detecting lever
18b Detecting protrusion
18c Injection needle detecting lever spring
18d Spring fixation lid
19 Injection needle detecting switch
20 Calendar
21 Timer
21A Embedded timer
22 Power supply section
23 Microprocessor
23A Storage section
24 Motor drive circuit
25 Current detecting circuit
26 Encoder
27 Display section
28 Sounder
29 Vibrator
30 Communication section
44a Powder formulation
44b Syringe convex part
44c Medicine solution
44d Rubber A
44e Rubber B

The invention claimed is:

1. A medicine injection device equipped with a formulation syringe which is previously containing a formulation and used to inject the formulation into a living body, the medicine injection device comprising:
a syringe detecting switch configured to detect replacement of the formulation syringe;
an injection needle detecting section configured to detect an attachment of an injection needle to the formulation syringe;
a microprocessor configured to check whether the formulation syringe is replaced during a time from the precedent attachment of the injection needle to the current attachment of the injection needle when the injection needle detecting section detects the attachment of the injection needle to the formulation syringe;
a timer configured to start counting a use time of the formulation syringe when the microprocessor confirmed the formulation syringe is replaced during a time from the precedent attachment of the injection needle to the current attachment of the injection needle;
a storage section which stores data of a predetermined term of expiration of the formulation from a start of use;
the microprocessor configured to check whether the use time exceeds the term of expiration of the formulation from the start of use; and
a notification section configured to notify warning that the term of expiration of the formulation from the start of use is over when the use time exceeds the term of expiration of the formulation from the start of use.

2. The medicine injection device according to claim 1, further comprising:
a remaining time calculation section which calculates a remaining time until the term of expiration of the formulation from the start of use based on the term of expiration of the formulation from the start of use and the use time counted by the timer, wherein the notification section notifies the remaining time until the term of expiration of the formulation from the start of use calculated by the remaining time calculation section.

3. The medicine injection device according to claim 2, wherein the notification section notifies the use time counted by the timer or the remaining time until the term of expiration of the formulation from the start of use by sound or voice.

4. The medicine injection device according to claim 2, wherein the notification section notifies by means of an alarm when the use time counted by the timer is more than a predetermined value or the remaining time until the term of expiration of the formulation from the date of use is a predetermined value or less.

5. The medicine injection device according to claim 1, further comprising:
a formulation injecting section which injects the formulation; and
a formulation injection preventing section which stops an operation of the formulation injecting section when it is determined that the term of expiration of the formulation syringe from the date of use is overdue based on the use time counted by the timer.

6. The medicine injection device according to claim 1, wherein the notification section is installed near a mounting part where the formulation syringe is mounted.

7. The medicine injection device according to claim 1, wherein the syringe detecting switch is brought into contact with one end of the formulation syringe when the formulation syringe is mounted on the medicine injection device.

8. The medicine injection device according to claim 1, further comprising a syringe cover detector which detects a formulation syringe cover by being brought into contact with one end of the formulation syringe cover when the formulation syringe is mounted on the medicine injection device.

9. The medicine injection device according to claim 1, wherein the injection needle detecting section includes:

an injection needle detecting lever which comes into contact with one end of an injection needle holding part when the injection needle is attached to a formulation syringe cover; and an injection needle detector which has a switch function to interlock with the injection needle detecting lever.

10. The medicine injection device according to claim 1, further comprising an input section for use in inputting information related to a time limit including the term of expiration of the formulation from the date of use, wherein the timer counts the use time based on the information related to the time limit.

\* \* \* \* \*